United States Patent [19]

Herlihy

[11] Patent Number: 4,478,936

[45] Date of Patent: Oct. 23, 1984

[54] IN VITRO ENZYMATIC PROCESS FOR PRODUCING GLUCURONIDES

[75] Inventor: Walter C. Herlihy, Cambridge, Mass.

[73] Assignee: Repligen Corporation, Cambridge, Mass.

[21] Appl. No.: 409,986

[22] Filed: Aug. 20, 1982

[51] Int. Cl.$^3$ .................. C12P 19/56; C12P 19/46; C12P 17/02; C12P 15/00

[52] U.S. Cl. .................................. 435/78; 424/65; 435/79; 435/123; 435/127; 435/136; 435/137; 435/195; 435/200

[58] Field of Search .................. 435/74, 78, 79, 97, 435/123, 127, 136, 137, 183, 193, 195, 196, 200, 201; 424/65

[56] References Cited

U.S. PATENT DOCUMENTS

| | | | |
|---|---|---|---|
| 3,240,777 | 3/1966 | Sarett et al. | 260/239.55 |
| 4,153,697 | 5/1979 | Hornke et al. | 424/258 |
| 4,292,250 | 9/1981 | Deluca et al. | 260/397.2 |

OTHER PUBLICATIONS

Ando, et al., Synthesis of Mycophenolic Acid $\beta$-D-Glucuronide and Its Antitumor Activity, J. Antibiotics, 23, 408–413, (1970).

Johnson, et al., Glucuronidation of Lipophilic Substrates, Prep. Biochem. 9, 391–406, (1979).

Primary Examiner—David M. Naff
Attorney, Agent, or Firm—Roman Saliwanchik

[57] ABSTRACT

An in vitro enzymatic process for preparing O-$\beta$-D-glucuronides which comprises reacting a solution of D-glucuronic acid with a solution of a compound which has a primary alcohol, and a solution of $\beta$-glucuronidase for a time sufficient to form the desired glucuronide. The glucuronides can be used for the following purposes: antiperspirants, cardiotonic agents, gastric acid inhibitors, vitamin D derivatives, treatment of psoriasis, and as antitumor agents.

4 Claims, No Drawings

IN VITRO ENZYMATIC PROCESS FOR PRODUCING GLUCURONIDES

DESCRIPTION

Background of the Invention

The preparation of β-glucuronides has been carried out by a number of different techniques. Chemical synthesis typically involves condensation of a suitably protected aglycon with an alkyl (2,3,4-tri-O-acetyl-α-D-glucopyranosyl halide) glucuronate followed by deprotection of the glucuronide and aglycon (Ando, K., Suzuki, S., and Arita, M. (1970) *J. Antibiotics* 23, 408; Sarett, L. H., Strachan, R. G., and Hirschmass, R. F. (1966) U.S. Pat. No. 3,240,777). A second approach involves feeding large amounts of the aglycon to animals, collecting their urine and isolating the glucuronide (Hornke, I., Fehlhaber, H. W., Uihlein, M. (1979) U.S. Pat. No. 4,153,697). Alternatively, the animal can be sacrificed and the bile isolated from its gall bladder, from which the glucuronide is purified (DeLuca, H. F., Schnoes, H. K., and LeVan, L. W. (1981) U.S. Pat. No. 4,292,250). This in vivo synthesis is catalyzed by the class of enzymes known as uridine diphosphoglucuronyl transferases. In vitro use of this enzyme to produce various β-glucuronides has been reported; for example, a phenolic compound has been glucuronidated (Johnson, D. B., Swanson, M. J., Barker, C. E., Fanska, C. B., and Murrill, E. E. (1979) *Prep. Biochem.* 9, 391).

An in vitro enzymatic process for the synthesis of β-glucuronides has several advantages over prior art chemical synthesis or animal feeding methods. Chemical synthesis requires a minimum of four steps: (1) protection of all the nucleophilic groups in the aglycon except the one involved in the glycosidic linkage, (2) preparation of a suitably protected reactive derivative of D-glucuronic acid, e.g., methyl (2,3,4-tri-O-acetyl-α-D-glucopyranosyl halide) glucuronate, (3) condensation, and (4) deprotection. Complications arise if the aglycon contains functional groups sensitive to the conditions of deprotection. For example, aglycons containing esters or other alkali-sensitive linkages can be hydrolyzed during the saponification of the methyl and acetyl protecting groups. In contrast, an in vitro enzymatic process involves a *single step* condensation between a readily available cofactor and the aglycon.

The animal feeding approach to making β-glucuronides also has several disadvantages as compared to an in vitro enzymatic method. The most significant disadvantage is that stringent purification is required. Other disadvantages are the inconvenience of maintaining animals, and other metabolic pathways including hydroxylation, alkylation, and sulfation can compete with glucuronidation, thus resulting in low yields of the desired product.

In a previous enzymatic in vitro process, I, as a joint inventor, was able to prepare for the first time essentially pure (+), (−) tropicamide O-β-D-glucuronide and the two diastereomers (+) tropicamide O-β-D-glucuronide and (−) tropicamide O-β-D-glucuronide. This invention comprised the incubation of liver microsomes in the presence of a suitable buffer to maintain the pH at about 7 to about 8.5, (+,−) tropicamide, and uridine 5'-diphosphoglucuronic acid (UDPGA), for a sufficient time for the glucuronidation to occur. This process was limiting to the extent that ester-containing anticholinergics, e.g., scopolamine, were not glucuronidated by the process.

By a subsequent invention, I was able to glucuronidate ester-containing anticholinergics. This in vitro enzymatic process comprised (1) removing substantially all esterases from liver microsomes, (2) incubating the treated liver microsomes in the presence of (a) a suitable buffer to maintain the pH at about 7 to about 8.5 (b) an ester-containing anticholinergic compound having a primary alcohol, and (c) uridine 5'-diphosphoglucuronic acid, for a sufficient time to conjugate the aglycon with glucuronic acid, and (3) isolating the desired O-β-D-glucuronic acid.

In the above two invention processes the use of the cofactor uridine 5'-diphosphoglucuronic acid (UDPGA) was essential. Since UDPGA is a relatively expensive material, its use in a commercial-type operation would be unfavorable. It would be advantageous to prepare the desired glucuronides by a process which could be adapted for commercial use. The process of the subject invention is such a process. It not only dispenses with the use of UDPGA by the use of a very inexpensive reactant, but, advantageously, it can be used to prepare the O-β-D-glucuronide of any compound containing a primary alcohol. Unexpectedly, the O-β-D-glucuronide of phenols cleavable by β-glucuronidase, as well as secondary and tertiary alcohols, cannot be prepared by the invention process. The process, as described herein, is the only known process which utilizes reversal of hydrolysis by β-glucuronidase in an in vitro biosynthetic reaction.

BRIEF SUMMARY OF THE INVENTION

Upon reacting a solution of D-glucuronic acid with a solution of a compound which has a primary alcohol, and a solution of β-glucuronidase for a time sufficient to form the glucuronide, there is obtained the O-β-D-glucuronide of said compound.

The glucuronides of any compound demonstrate enhanced water solubility. This property can be advantageous for the pharmaceutical use of medicinals, for example, mycophenolic acid glucuronide. See U.S. Pat. Nos. 3,777,020 and 3,758,455.

The glucuronides of anticholinergics are useful as antiperspirants. These glucuronides do not demonstrate the undesirable mydriatic property of the anticholinergics. This then overcomes one of the problems in the use of anticholinergics as antiperspirants.

A further advantageous property of the glucuronides is that their antiperspirant activity is not destroyed by the esterase activity in human perspiration, at least not to the extent that it is destroyed in the nonglucuronidated compounds.

The glucuronides can be formulated for antiperspirant use by use of well-known ingredients and procedures. For example, the formulations and procedures disclosed in U.S. Pat. Nos. 3,624,200 and 3,767,786 can be used by substituting the glucuronides for the antiperspirant compounds disclosed in these patents.

Other uses for glucuronides are as cardiotonic agents (U.S. Pat. No. 4,335,131); vitamin D derivatives (U.S. Pat. No. 4,292,250); gastric acid secretion inhibitors (European Patent Application No. 52-074); treatment of psoriasis (U.S. Pat. No. 3,777,020); and as antitumor agents (U.S. Pat. No. 3,758,455).

DETAILED DESCRIPTION OF THE INVENTION

The in vitro enzymatic process of the subject invention is stereospecific. It utilizes a readily available enzyme, i.e., β-glucuronidase, and the inexpensive reactant glucuronic acid, to yield useful β-glucuronides. More specifically, a solution of glucuronic acid is reacted with a solution of a compound, e.g., tropicamide, scopolamine, hyoscyamine, atropine, and like acceptor substrates which have a primary alcohol, and a solution of β-glucuronidase, to give the O-β-D-glucuronide of said compound.

Any β-glucuronidase can be used in the process, e.g., E. coli, bovine liver, Mollusk, and the like. These named are perhaps the most readily available β-glucuronidases.

A wide range of concentration of reactants can be used in the process so long as the particular reactant is in solution. Advantageously, the higher the concentration of glucuronic acid, the higher the yield of the desired O-β-D-glucuronide.

The temperature of incubation in the enzymatic step can be from about 20° to about 45° C.

The enzymatic reaction, described herein, can be carried out over a pH range of about 3.8 to about 10.0 with different buffer strengths and with various buffers, for example, sodium phosphate, sodium N-2-hydroxyethyl piperazine-N'-2-ethanesulfonic acid, tris hydrochloride, 3-tris-hydroxymethyl methylamino propanesulfonic acid, and the like.

The chromatographic methods described herein are based on reversed phase liquid chromatography on C-18 silica supports. This technique is well suited for the purification of enzymatically-produced glucuronides of hydrophobic compounds. Unreacted aglycon is much more hydrophobic than the corresponding glucuronide and thus will be well resolved on reversed phase systems. Glucuronic acid is very hydrophilic and wil be much less retained than the glucuronide of a hydrophobic compound. Finally, all the solvent systems described are based on $NH_4OAc$, a volatile buffer. Modifications to this system may be necessary in order to purify glucuronides of very hydrophilic compounds. Other reversed phase stationary supports, for example, phenyl silica, C-8 silica, and the like, can be used. The resolution of the two diastereomers of tropicamide O-β-D-glucuronic acid is enhanced when the pH is lowered from 7.0 to 3.7, which would increase the fraction of the molecules in the zwitterionic form necessary for an intramolecular ionic interaction. In addition, increasing the ionic strength from 0.1% $NH_4OAc$ to 1% $NH_4OAc$ diminishes the resolution as would be expected if an intramolecular "salt bridge" were present.

The following examples are illustrative of the process of the invention, but are not to be construed as limiting. All percentages are by weight and all solvent mixture proportions are by volume unless otherwise noted.

EXAMPLE 1

Synthesis of (+,−) Tropicamide O-β-D-Glucuronic Acid

A 1.7M sodium D-glucuronic acid stock solution is prepared by adding 16.5 gm of glucuronic acid to 40 ml of 50 mM sodium phosphate buffer; the pH is adjusted to ~6.8 with 5N NaOH, and the final volume is adjusted to 50 ml with 50 mM sodium phosphate (pH=6.8).

A 300 μl enzyme reaction is prepared by combining 100 μl of the 1.7M solution of sodium D-glucuronic acid, 100 μl of a 5 mg/ml solution of tropicamide, 30 μl of a 0.5M solution of sodium phosphate (pH=6.8), 50 μl of water and 20 μl of a 1000 Unit/ml solution of freshly dissolved E. coli β-glucuronidase (E.C. 3.2.1.31) (Sigma Type III, Sigma Chemical Co., St. Louis, Mo.). Immediately after addition of the enzyme, a 25 μl aliquot is removed and incubated at 70° C. for 1 min. to inactivate the enzyme. A second aliquot is removed after a 20 hr. incubation at 37° C. Both samples are diluted with an equal volume of 0.1% $NH_4OAc$ (pH=5.75) and analyzed by high pressure liquid chromatography (HPLC) as follows: a 0.39×30 cm C-18 μBondapak column (Waters Associates, Milford, Mass.) is eluted at 2 ml/min. with 0.1% $NH_4OAc$ (pH=5.75). After injection of the sample, a linear gradient to 60% methanol is applied to the column over a 20 minute period. The column eluant is monitored with an ultraviolet detector set at 254 nm. Approximately 1% of the (+,−) tropicamide is converted to the corresponding O-β-D-glucuronic acid derivative.

EXAMPLE 2

Separation of (+) and (−) Tropicamide O-β-D-Glucuronide

The two isomers are isolated from a mixture as follows:

The two isomers are isolated by HPLC on a 0.39×30 cm column of C-18 μBondapak (Waters Associates). The column is equilibrated with 0.013M $NH_4OAc$ (pH=3.7) containing 10% methanol at a flow rate of 2 ml/min. One minute after injection of the sample, the percentage of methanol in the eluant is raised to 22% in one minute. The two diastereomers elute at about eleven and thirteen minutes respectively. Retention times vary with column condition and the optimal concentration of methanol is normally determined with analytical injections. The two diastereomers are obtained in their essentially pure form.

Characterization of (+) and (−) Tropicamide O-β-D-Glucuronide

The two reaction products (50 μg in 150 μl of 50 mM sodium phosphate, pH=6.8) are individually treated with ten Fishman units of E. coli β-glucuronidase (E.C. 3.2.1.31) at 37° C. for 1 hour. Both compounds are quantitatively hydrolyzed by the glucuronidase to products which were indistinguishable by HPLC from the starting material, (+,−) tropicamide, in the 0.1% $NH_4OAc$ (pH=5.75)/methanol solvent system described above. The products are also indistinguishable from (+,−) tropicamide when chromatographed on C-18 in a second solvent system consisting of 1% triethylammonium acetate (pH=7.0) eluted with a linear gradient to 50% acetonitrile in 25 minutes. These data show that both products contain an intact tropicamide moiety. The known specificity of this enzyme shows the presence of a glucuronic acid moiety and shows that the glycosidic linkage has the β configuration. The tropicamides released by glucuronidase treatment are individually converted back to the corresponding glucuronides using the conditions described above. These reactions produced single products, i.e., the tropicamide derived from glucuronidase treatment of component 1 yields only component 1, and the tropicamide derived from component 2 yields only component 2. Thus the two products are diastereomers which differ only in the configuration of the optically active carbon in the tropicamide moiety.

The products of β-glucuronidase hydrolysis are further characterized by their rotation of 589 nm plane polarized light. These measurements show that the component which elutes earlier in the HPLC assay is dextrorotatory and the later eluting compound is levorotatory. Experiments with lesser amounts of *E. coli* glucuronidase show that the hydrolysis rate of (+) tropicamide O-β-D-glucuronide is approximately twice as rapid as (−) tropicamide O-β-D-glucuronide.

The ultraviolet spectra of (+), (−) tropicamide, (+) tropicamide O-β-D-glucuronide, and (−) tropicamide O-β-D-glucuronide are recorded in a 0.05% NH4OAc (pH=7.0) solution. All three samples have identical spectra with maxima at 257 nm (Emax=2140) and shoulders at 252 nm and 263 nm characteristic of a para substituted pyridone moiety.

The molecular weights of the two diastereomers are determined by direct chemical ionization (DCI) mass spectrometry and fast atom bombardment (FAB) mass spectrometry. The ammonia DCI spectrum of each isomer gives a quasi molecular ion at m/z=461 (M+H)+, confirming the molecular weight as 460. Similarly the zenon FAB spectrum of both isomers contains a series of ions at m/z=461 (M+H)+, m/z=483 (M+Na)+, and m/z=499 (M+K)+ clearly showing a molecular weight of 460.

The infrared spectra in KBr pellets of the two tropicamide glucuronides both exhibit strong absorption bands centered at 3150 cm$^{-1}$ and 1400 cm$^{-1}$ confirming that the ammonium salt had been formed as expected. Both compounds also exhibit a broad band at 1600 cm$^{-1}$ which is consistent with the presence of both a carboxylate and a tertiary amide carbonyl. In addition, a shoulder at 3350 cm$^{-1}$ is consistent with the hydroxyl groups in the glucuronides.

The ammonium and other base salts of the compounds are useful in the same manner as the free acid form. If desired the ammonium salt can be converted to the free acid by means well known in the art, for example, by adjusting the pH of the ammonium salt solution with a weak acid so as not to cause hydrolysis of the diastereomer. Salts with both inorganic and organic bases can be formed with the free acid. For example, in addition to ammonium salt, there also can be formed the sodium, potassium, calcium, and the like, by neutralizing an aqueous solution of the free acid.

EXAMPLE 3

Synthesis of Scopolamine O-β-D-Glucuronic Acid

To a vial containing 1000 Units of lyophilized *E. coli* β-glucuronidase is added 300 μl of a 100 mg/ml solution of scopolamine, 2.4 ml of the 1.7M sodium glucuronic acid stock solution described in Example 1, and 300 μl of a 0.5M sodium phosphate solution (pH=6.8). Samples (50 μl) are taken immediately after mixing and after a 20 hr incubation at 37° C. The enzyme is inactivated by heating as described in Example 1. Samples are diluted with an equal volume of 0.1% NH4OAc (pH=7.5) and analyzed by HPLC using the system described in Example 2.

Characterization of Scopolamine O-β-D-Glucuronic Acid

The reaction product (150 μg in 450 μl of 50 mM sodium phosphate, pH=6.8) is treated with 150 Fishman units of *E. coli* β-glucuronidase (E.C. 3.2.1.31) at 37° C. for two hours. The compound is quantitatively hydrolyzed by the glucuronidase to a product which is indistinguishable by HPLC from the starting material, scopolamine, in the 0.1% NH4OAc (pH=7.5)/methanol solvent system described above. The glucuronidase product is also indistinguishable from scopolamine when chromatographed on C-18 in a second solvent system consisting of 1% triethylammonium acetate (pH=7.0) eluted with a linear gradient to 50% acetonitrile in 25 minutes. Since the chromatographic behavior of scopolamine is markedly affected by pH in the range of pH=5.8, the hydrolysis product is chromatographed in a third solvent system consisting of 0.1% NH4OAc (pH=5.0) eluted with a linear gradient to 50% acetonitrile in 25 minutes and found to be identical to scopolamine. These data indicate that the product contains an intact scopolamine moiety. The known specificity of this enzyme indicates the presence of a glucuronic acid moiety and indicates that the glycosidic linkage has the β configuration.

The ultraviolet spectrum of the reaction product is recorded in a 0.05% NH4OAc (pH=7.0) and compared to the spectrum of scopolamine. Both compounds exhibit maxima at 252 nm, 258 nm, and 263.5 nm, and a strong end absorption beginning at ~240 nm, indicating that the glucuronide contains an intact tropic acid moiety.

The molecular weight of the product is determined by fast atom bombardment (FAB) mass spectrometry. The xenon FAB spectrum contained a single ion at m/z=480 (M+H)+, clearly indicating a molecular weight of 479. The exact mass of the (M+H)+ ion is determined by peak matching to be 480.186, which is in excellent agreement with the mass expected for a compound with this elemental composition, 480.187.

Esterase Cleavage of Scopolamine and Scopolamine O-β-D-Glucuronic Acid

To 150 μl of 150 mM tris HCl (pH=8.0) solution containing 0.7 mM scopolamine and an equimolar amount of scopolamine O-β-D-glucuronic acid is added 1 mg of unwashed rabbit UDPGA-dependent glucuronyl transferase. Immediately after addition of the enzyme, 50 μl are removed and incubated at 70° C. for 1 minute and centrifuged at 14,000 g for 5 minutes. The supernatant (40 μl) is removed; 4 μl of 1% NH4OAc (pH=7.5) is added, and the sample is analyzed by HPLC using the 0.1% NH4OAc (pH=7.5)/methanol solvent system described above. A second 50-μl sample is prepared and analyzed after a 2-hour incubation at 37° C.

EXAMPLE 4

Synthesis of Tropicamide O-β-D-Glucuronic Acid with Bovine Liver β-Glucuronidase A 1.2 ml solution containing 0.85M glucuronic acid, 4 mg/ml tropicamide, 48,000 Units of bovine liver β-glucuronidase (Sigma Type B-1, Sigma Chemical Co., St. Louis, Mo.) and 50 mM NaOAc (pH=5.0) is incubated at 37° C. After 20 hr. 50 μl is removed and heated at 70° C. for one minute, spiked with 5 μl of 1%

NH4OAc (pH=7.5) and analyzed by HPLC using the conditions described above for the analysis of scopolamine glucuronic acid. The product of the reaction has an identical retention time as standard (+,−) tropicamide O-β-D-glucuronic acid. Approximately 5 μg of product is isolated by HPLC of which 2 μg is dissolved in 122 μl of 50 mM sodium phosphate (pH=6.8), to which is added 122 μl of a 1000 Unit/ml solution of *E. coli* β-glucuronidase. The product is quantitatively converted to tropicamide after a 10 min incubation at 37° C. judged by HPLC analysis.

EXAMPLE 5

Synthesis of Tropicamide O-β-D-Glucuronic Acid with Mollusk β-Glucuronidase

A one ml solution containing 4 mg tropicamide and 1.2M glucuronic acid is adjusted to pH=3.8 with concentrated hydrochloric acid. This solution is combined with a one ml solution containing 4064 Units of Abalone β-glucuronidase (Sigma) in 50 mM sodium acetate (pH=3.8). After a 16 hr incubation, a 50 μl aliquot is heated and analyzed by HPLC as described above for the bovine β-glucuronidase reaction. A product peak with a retention time equal to that of a tropicamide O-β-D-glucuronic acid standard is observed.

EXAMPLE 6

Upon substituting atropine in Example 1 for tropicamide, there is obtained atropine O-β-D-glucuronic acid.

EXAMPLE 7

Upon substituting hyoscyamine in Example 1 for tropicamide, there is obtained hyoscyamine O-β-D-glucuronic acid.

Characterization of Hyoscyamine O-β-D-Glucuronic Acid

The HPLC system used to assay the synthesis of hyoscyamine O-β-D-glucuronic acid consists of a linear gradient from 0.1% NH4OAc (pH=5.75) to 60% methanol in twenty minutes. All other parameters are identical to the chromatography described above for scopolamine. Under these conditions the hyoscyamine elutes slightly after scopolamine, and the product of the transferase reaction elutes slightly after scopolamine O-β-D-glucuronic acid, indicating that the expected glucuronide is formed. This product is purified by HPLC. Approximately 40 μg is dissolved in 400 μl of 50 mM sodium phosphate (pH=6.8) containing 1000 U/ml of *E. coli* β-glucuronidase. Immediately after addition of the enzyme and after a one-hour incubation at 37° C., 50-μl aliquots are removed, heated at 70° C. for 1 minute and analyzed by HPLC. The aglycon released from the glucuronide and hyoscyamine have identical retention in the 0.1% NH4OAc (pH=5.75)/methanol solvent system described above.

EXAMPLE 8

Upon substituting other acceptor substrates which have a primary alcohol for tropicamide in Example 1, there is obtained the corresponding glucuronide of the acceptor substrate used in the reaction.

EXAMPLE 9

Upon substituting any anticholinergic having a primary alcohol for tropicamide in Example 1, there is obtained the corresponding glucuronide of said anticholinergic.

EXAMPLE 10

Salts with both inorganic and organic bases can be formed with the free acid of the compounds prepared by the subject invention process. For example, in addition to the ammonium salt, there also can be formed the sodium, potassium, calcium, and the like, by neutralizing an aqueous solution of the free acid with the corresponding base. The ammonium and other base salts of the compounds are useful in the same manner as the free acid form.

I claim:

1. An in vitro enzymatic process for preparing the O-β-D-glucuronide of an anticholinergic compound which has a primary alcohol, which comprises reacting a solution of D-glucuronic acid with a solution of said compound, and a solution of β-glucuronidase, for a time sufficient to form the O-β-D-glucuronide, and isolating said glucuronide.

2. A process, according to claim 1, wherein said anticholinergic compound is selected from the group consisting of tropicamide, scopolamine, atropine and hyoscyamine.

3. An in vitro enzymatic process for preparing the O-β-D-glucuronide of tropicamide which comprises reacting a solution of D-glucuronic acid with a solution of tropicamide, and a solution of β-glucuronidase, for a time sufficient to conjugate the tropicamide with glucuronic acid, and isolating (+,−) tropicamide O-β-D-glucuronic acid.

4. An in vitro enzymatic process for preparing the O-β-D-glucuronide of scopolamine which comprises reacting a solution of D-glucuronic acid with a solution of scopolamine, and a solution of β-glucuronidase, for a time sufficient to conjugate the scopolamine with glucuronic acid, and isolating scopolamine O-β-D-glucuronic acid.

* * * * *